US00PP30286P2

(12) United States Plant Patent
Selinger

(10) Patent No.: US PP30,286 P2
(45) Date of Patent: Mar. 12, 2019

(54) ***SYRINGA* PLANT NAMED 'BAILBRIDGET'**

(50) Latin Name: *Syringa hybrid*
Varietal Denomination: Bailbridget

(71) Applicant: Bailey Nurseries, Inc, Newport, MN (US)

(72) Inventor: Donald R. Selinger, Woodbury, MN (US)

(73) Assignee: BAILEY NURSERIES INC, Newport, MN (US)

( * ) Notice: Subject to any disclaimer, the term of this patent is extended or adjusted under 35 U.S.C. 154(b) by 0 days.

(21) Appl. No.: 15/731,268

(22) Filed: May 15, 2017

(51) Int. Cl.
*A01H 5/02* (2018.01)

(52) U.S. Cl.
USPC ..... Plt./248

(58) Field of Classification Search
USPC ..... Plt./248
See application file for complete search history.

*Primary Examiner* — Keith O. Robinson
(74) *Attorney, Agent, or Firm* — Penny J. Aguirre

(57) ABSTRACT

A new cultivar of *Syringa* plant named 'Bailbridget' that is characterized by its compact and upright plant habit, its double flowers that are deep violet in color, newly emerging foliage that is flushed purple in color and mature foliage that is dark green in color, its new growth stems that are purple in color, and its good resistance to powdery mildew.

2 Drawing Sheets

Botanical classification: *Syringa* hybrid.
Variety denomination: 'Bailbridget'.

BACKGROUND OF THE INVENTION

The present invention relates to a new and distinct cultivar of *Syringa* hybrid and will be referred to hereafter by its cultivar name, 'Bailbridget'. 'Bailbridget' is a new cultivar of lilac grown for use as an ornamental landscape plant.

'Bailbridget' arose from an on going breeding program conducted by the Inventor in Cottage Grove, Minn. The objective of the breeding program was to develop a new cultivar of *Syringa* with double flowers, disease resistance, and foliage and stems that are tinted purple in color.

'Bailbridget' originated from a cross made by the Inventor in May of 2001 between *Syringa vulgaris* 'Charles Joly' (not patented) as the female parent that was pollinated with a mixture of pollen collected from *Syringa* 'Old Glory' (not patented) and *Syringa* 'Declaration' (not patented). The Inventor selected 'Bailbridget' as a single unique plant amongst the seedlings that resulted from the above cross in May of 2007.

Asexual propagation of the new cultivar was first accomplished by stem cuttings in June 2008 under the direction of the Inventor in Cottage Grove, Minn. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailbridget' as a unique cultivar of *Syringa*.

1. 'Bailbridget' exhibits a compact and upright plant habit.
2. 'Bailbridget' exhibits double flowers that are deep violet in color.

3. 'Bailbridget' exhibits newly emerging foliage that is flushed purple in color and mature foliage that is dark green in color.
4. 'Bailbridget' exhibits new growth stems that are purple in color.
5. 'Bailbridget' exhibits good resistance to powdery mildew.

The female parent of 'Bailbridget', 'Charles Joly' differs from 'Bailbridget' in having a taller and wider plant size, in having flowers that are magenta in color and in having new foliage and new stem growth that is green in color. The possible male parent of 'Bailbridget', 'Old Glory', differs from 'Bailbridget' in having a taller and wider plant size, a rounder plant habit, single flowers that are blue-purple in color, and in having new stem and leaves that are green in color. The other possible male parent of 'Bailbridget', 'Declaration', differs from 'Bailbridget' in having flowers that are red-purple in color and and in having new stem and leaves that are green in color. The new *Syringa* can be most closely compared to the cultivars *Syringa* x *hyacintaflora* 'Pocahontas' (not patented) and *Syringa vulgaris* 'President Grevy' (not patented). 'Pocahontas' is similar to 'Bailbridget' in having flowers that are violet in color and foliage that is dark green in color. 'Pocahontas' differs from 'Bailbridget' in having a taller and wider plant size, single flowers, and in having new stem and leaves that are green in color. 'President Grevy' is similar to 'Bailbridget' in having an upright plant habit and double flowers. 'President Grevy' differs from 'Bailbridget' in having a taller and wider plant size and flowers that are lilac-blue in color.

BRIEF DESCRIPTION OF THE DRAWINGS

The accompanying colored photographs illustrate the overall appearance and distinct characteristics of the new *Syringa*. The photographs were taken of a plant about 7 years in age as grown outdoors at a nursery in Cottage Grove, Minn.

The photograph in FIG. 1 provides a side view of a plant of 'Bailbridget' in bloom.

Figure 1:
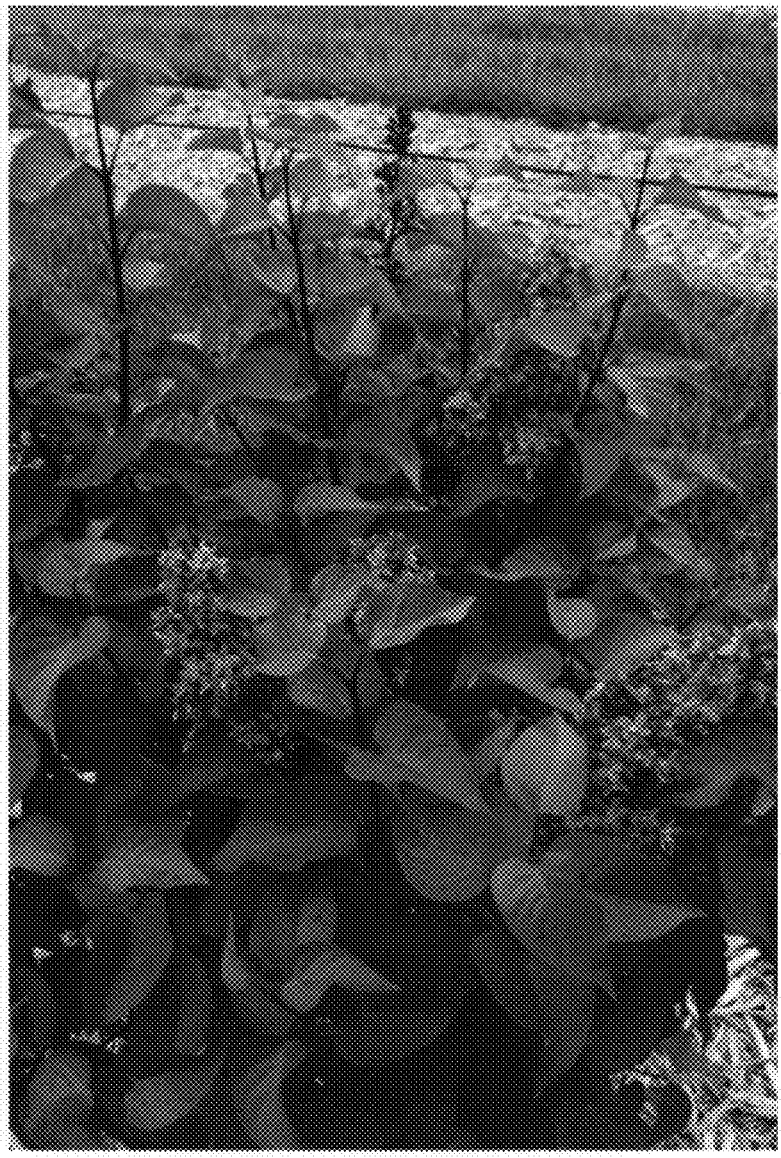
Figure 2:
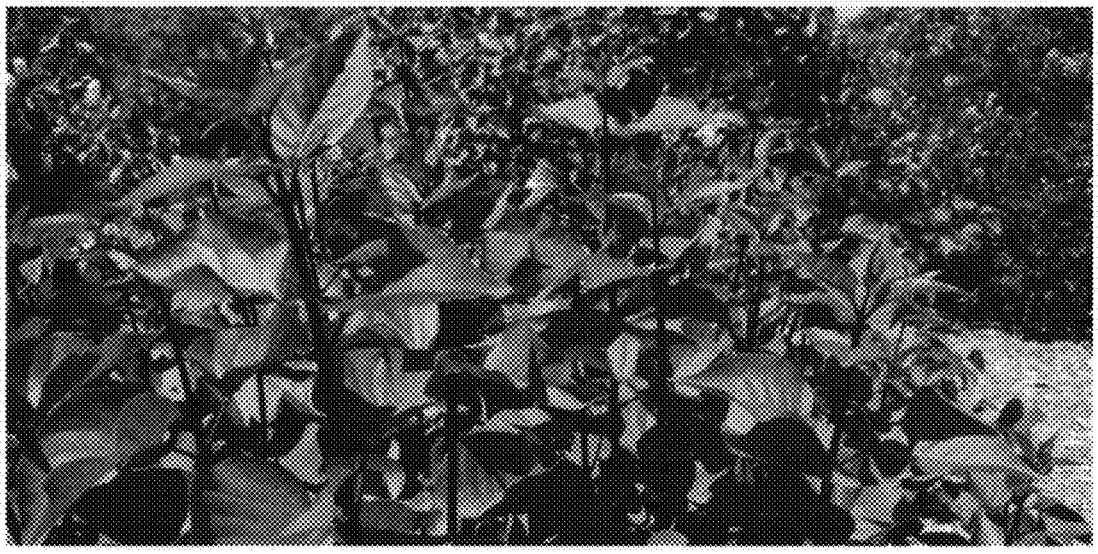

The photograph in FIG. 2 provides a close-up view of the new foliage of 'Bailbridget'.

The colors in the photographs are as close as possible with the photographic and printing technology utilized and the color values cited in the detailed botanical description accurately describe the colors of the new *Syringa*.

DETAILED BOTANICAL DESCRIPTION

The following is a description of 7 year-old plants as grown outdoors in the ground in Newport, Minn. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—2 weeks starting in mid-May in Cottage Grove, Minn.

*Plant type.*—Deciduous shrub.

*Plant habit.*—Compact and upright.

*Height and spread.*—1.8 to 2.43 m in height and 1.5 to 2.13 m in width as a mature plant in the landscape.

*Cold hardiness.*—At least to U.S.D.A. Zone 3.

*Diseases.*—Good resistance to powdery mildew (caused by *Erysiphe syringae*) has been observed.

*Root description.*—Fibrous and dense, a blend of 158A and 161A in color.

*Propagation.*—Softwood stem cuttings.

*Growth rate.*—Moderate.

*Root development.*—Cuttings root readily; a 2-inch liner will fully root in about 3 months.

Branch description:

*Branch shape.*—Rounded.

*Branch color.*—Young new growth; N77A, mature 1 year and older and and main stems; a blend of 202B and 199B.

*Branch size.*—5 main branches up to 79 cm in length and up to 2 cm in diameter at base, lateral branches 25 cm in length and 6 mm in diameter, new growth 24 cm in length and 4 mm in diameter.

*Branch surface.*—Young new growth sparsely pubescent, main stems and mature lateral stems smooth barked, matte, moderately to densely covered with lenticels; an average of 30 lenticels per stem that is 2 cm in length, 155A in color, 1 mm in diameter.

*Internode length.*—An average of 4 cm.

*Branching.*—Multi-branched, main stems (average of 5) nearly upright, lateral branches (2 to 5 per main stem) and new growth (and average of 4 per lateral branch) upright to 20° to vertical.

*Stipules.*—None.

*Dormant buds.*—Imbricate, 2 mm in length, 1.5 mm in width, 165A in color.

Foliage description:

*Leaf shape.*—Ovate.

*Leaf division.*—Simple.

*Leaf base.*—Cordate.

*Leaf apex.*—Acuminate.

*Leaf fragrance.*—None.

*Leaf venation.*—Pinnate, upper surface matches leaf color and flushed at midrib with 183A, midrib 144B, other veins match leaf color.

*Leaf margins.*—Entire

*Leaf arrangement.*—Opposite.

*Leaf attachment.*—Petiolate.

*Leaf surface.*—Young; both surfaces are glossy, mature; upper and lower surface glabrous and slightly satiny.

*Leaf size.*—An average of 6.5 cm in length and width.

*Leaf quantity.*—20 leaves per young branch 24 cm in length.

*Leaf color.*—Young leaves upper and lower surface; 146A flushed with 183A with thin margin of 183A, mature leaves upper surface; 146A, mature leaves lower surface; 146B, fall color; same as mature foliage until drop.

*Petioles.*—An average of 2 cm in length and 2 mm in width, 144B on both surfaces and flushed with 183A on upper surface, surface slightly pubescent.

Inflorescence description:

*Inflorescence type.*—Thyrse compound panicles on terminals and laterals of previous years' growth, oblong to slightly ovate in overall shape.

*Inflorescence size.*—16 cm in length, 9 cm in width.

*Density of flowers of the inflorescence.*—Dense.

*Rachis.*—Rounded in shape, average of 15 cm in length and 2 mm in width, 147A flushed with N200A in color, surface is glossy and sparsely pubescent, rachis leaves; an average of 10 leaves per rachis, 1.5 cm in length, 5 mm in width, narrowly elliptic in shape, truncate base, acuminate tip, both surfaces are similar to leaf foliage in color. veins and surface description.

*Peduncles.*—Slightly flattened to round in shape, an average of 6 cm in length and 2 mm in width, 147A and lightly flushed with 200A in color, glossy and sparsely pubescent surface, moderate strength.

*Pedicels.*—Round in shape, an average of 4 mm in length and 0.5 mm in width, 147A in color, lightly flushed with 200A in color, glossy and sparsely pubescent surface, moderate strength.

*Flower buds.*—Orbicular apex with tubal base, an average of 5 mm in width, 1 cm in depth, N77B in color.

*Flower fragrance.*—Pleasant and strong lilac scent.

*Persistence of flowers.*—Self-cleaning, calyx persistent.

*Lastingness of flowers.*—Individual panicles bloom for about 2 weeks, depending on temperature.

*Flower quantity.*—An average of 200 flowers per compound panicle.

*Flower type.*—Double, salverform with spreading petal lobes.

*Flower aspect.*—Upwards and outward.

*Flower size.*—An average of 2 cm in diameter and depth.

*Petals.*—4 outer lobes and 4 inner lobes and fused to tube, lobes: average of 9 mm in length and 6 mm in width, broadly elliptic in shape, broadly acute apex, entire margins, base cuneate to fused point on tube, both surfaces glabrous and slightly satiny, upper petal lobes primarly horizontal with medium undulation and lower petal lobes slightly recurved with medium undulation, color opening upper and lower surfaces; N77B and suffused with 77B and 77C and blending to 155A at base, color mature upper and lower surfaces; blend of 77B and 77C and blending to to 155A at base, tube; an average of 9 mm in length and 1.5 mm in width, glabrous and slightly satiny surface, color when opening outer surface N77B, color when mature outer surface 77B, color of inner surface when opening N77B, color of inner surface when mature; N77C with margins 155A.

*Petaloids.*—0 to 2, spatulate in shape an often curled into center of flower, glabrous surface, acute margin, base linear, color of both surfaces opening and mature; a blend of 76A, 76B, and 76C.

*Calyx.*—Campanulate, about 3 mm in width, 2 mm in depth, comprised of 4 fused sepals with tips unfused with acute apices, surface is glossy, 147A in color.

Reproductive organs:

*Presence.*—Flowers range from perfect to pistillate with petaloids pistillate or with one stamen and one pistil.

*Pistils.*—1, average of 5 mm in length, stigma; bi-fid, 1.5 mm in length, 145D in color, style; 2.5 mm in length, 145D in color, ovary; oval in shape, 2 mm in length, superior and 144C in color.

*Stamens.*—0 to 2, anthers; an average of 1 mm in width, 2 mm in length, ovate in shape, 8A in color, filaments; 2 to 4 mm in length, 1.5 mm in width, NN155A in color, pollen; none observed.

*Fruit and seed.*—Not oberved to date.

It is claimed:

1. A new and distinct cultivar of *Syringa* plant named 'Bailbridget' as herein illustrated and described.

* * * * *